United States Patent
Pines et al.

(10) Patent No.: US 7,477,947 B2
(45) Date of Patent: Jan. 13, 2009

(54) SYSTEM AND METHOD FOR ELECTRICAL STIMULATION OF SALIVATION

(76) Inventors: Erella Pines, P.O. Box 1745, Pardes Hanna 37110 (IL); Mark Fenster, Herzog 11/10, Raanana 43364 (IL)

(\*) Notice: Subject to any disclaimer, the term of this patent is extended or adjusted under 35 U.S.C. 154(b) by 376 days.

(21) Appl. No.: 10/500,013

(22) PCT Filed: Jan. 30, 2002

(86) PCT No.: PCT/IL02/00085

§ 371 (c)(1),
(2), (4) Date: Jun. 23, 2004

(87) PCT Pub. No.: WO02/060522

PCT Pub. Date: Aug. 8, 2002

(65) Prior Publication Data

US 2005/0090864 A1 Apr. 28, 2005

Related U.S. Application Data

(60) Provisional application No. 60/264,686, filed on Jan. 30, 2001.

(51) Int. Cl.
*A61N 1/18* (2006.01)

(52) U.S. Cl. .............................. 607/134; 607/2; 607/62; 600/554

(58) Field of Classification Search ................. 607/134, 607/2, 116, 72, 62; 600/554
See application file for complete search history.

(56) References Cited

U.S. PATENT DOCUMENTS

| 527,037 | A | * | 10/1894 | Funk | 433/167 |
| 3,942,535 | A | * | 3/1976 | Schulman | 607/33 |
| 4,244,373 | A | * | 1/1981 | Nachman | 607/9 |
| 4,519,400 | A | * | 5/1985 | Brenman et al. | 600/554 |
| 5,188,104 | A | * | 2/1993 | Wernicke et al. | 607/40 |
| 5,190,053 | A | * | 3/1993 | Meer | 607/134 |
| 5,326,349 | A | * | 7/1994 | Baraff | 623/9 |
| 5,760,692 | A | * | 6/1998 | Block | 340/573.1 |
| 5,792,210 | A | * | 8/1998 | Wamubu et al. | 607/58 |
| 6,067,474 | A | * | 5/2000 | Schulman et al. | 607/57 |
| 6,230,052 | B1 | * | 5/2001 | Wolff et al. | 607/2 |
| 6,239,705 | B1 | * | 5/2001 | Glen | 340/573.1 |
| 6,895,280 | B2 | * | 5/2005 | Meadows et al. | 607/46 |

FOREIGN PATENT DOCUMENTS

WO WO 00/44439 * 8/2000

\* cited by examiner

*Primary Examiner*—Mark W Bockelman
*Assistant Examiner*—Eric D Bertram

(57) ABSTRACT

A system, a device and a method for electrically detecting a lack of saliva in an oral cavity of an individual and for electrically stimulating the oral cavity so as to induce production of saliva from at least one salivary gland are disclosed. The system includes a control device for detecting a measure of salivation in the individual and for delivering electrical impulses to the oral cavity of the individual, a check device for checking a state of the control device and for modifying at least one parameter of the control device, and, a computer device for exchanging information with the check device.

5 Claims, 12 Drawing Sheets

SYSTEM AND METHOD FOR ELECTRICAL STIMULATION OF SALIVATION

REFERENCE TO RELATED APPLICATIONS

This application claims the benefit of priority of PCT application PCT/IL02/00085 filed Jan. 30, 2002, which in turn claims the benefit of priority to U.S. provisional application No. 60/264,686 filed Jan. 30 2001.

FIELD AND BACKGROUND OF THE INVENTION

The present invention relates to a system and method for electrical stimulation of salivation and, more particularly, to a system and a method of using same for electrically detecting a lack of saliva in the oral cavity and for electrically stimulating the oral cavity so as to induce the production of saliva from the salivary glands.

Saliva performs many critical functions in the oral cavity and is essential for the maintenance of oral health. The accomplishment of the functions of saliva depends on proper salivary production. Saliva neutralizes acid that promotes dental caries and aids in the remineralization of areas of incipient caries development. Saliva contains specific antifungal agents and reduces bacteria in the oral cavity by a number of means including dilution, aggregating factors, and microbicidal enzymes. Salivary glycoproteins reduce intraoral trauma (between different oral structures such as teeth, cheek, tongue and lips) by lubricating the hard and soft tissues and saliva aids swallowing by facilitating bolus formation. Salivary enzymes such as lipase and amylase start the digestion of food. Taste perception is facilitated by salivary dilution and delivery of food particles to the taste buds.

Saliva is produced by the salivary glands. Each individual has three pairs of salivary glands: the parotid glands (the largest, which lie under the skin of the cheeks), and the submandibular and the sublingual, which are located at the floor of the mouth. The secretion of saliva is regulated by the autonomic nervous system.

Xerostomia, or dry mouth, is a very common complaint. While between 20-30% of the adult population may complain of it at some time, for 1-2% of the population it is a serious problem. The chronic lack of saliva is associated with rampant, severe dental caries, difficulty chewing, painful swallowing, diminished taste and smell, and oral fungal infections.

Xerostomia can result from many different causes. The most prevalent is as a side effect of one or more medications that inhibit salivation through anticholinergic or other mechanisms. Hundreds of drugs are known to have this side effect, especially antidepressants, MAO inhibitors, neuroleptics, parasympatholytics, some analgesics and certain combinations of anti-hypertensive agents. A variety of autoimmune disorders, particularly, Sjogren's syndrome, are another important cause. One to three million Americans suffer from Sjogren's syndrome. Severe salivary gland hypofunction also results from therapeutic irradiation of the head and neck as well as other causes including other diseases such as sarcoidosis, amyloidosis, graft-versus-host disease, HIV infection, diabetes, Alzheimer disease, depression, dysautonomia and Fabry disease. Aging itself appears to be a cause of xerostomia as well.

Treatment of xerostomia is difficult and while there are some currently available treatments, they are not satisfactory. Symptomatic treatments include sialogogues such as sugarless hard candies or chewing gum. Symptomatic palliative relief can sometimes be obtained by frequent sips of water or use of a saliva substitute. In patients whose xerostomia has a non-pharmacologic cause, oral pilocarpine (if not contraindicated) may be helpful but has the side effects of perspiration, flushing, urinary urgency and lacrimation.

It is well known that it is possible to increase salivation by stimulation of the salivary glands by low power electric current. Studies have demonstrated that the salivary glands respond to discrete stimulatory pulses with increased salivation (Weiss et al J Oral Maxillo-facial Surg 44:845-50, 1996; Steller et al J Dental Res 67: 1334-7, 1988; Talal et al Rheum Int 12:43-5, 1992)

U.S. Pat. Nos. 4,519,400 and 4,637,405 to Brenman et al teach a device and method for electrical induction of salivation. The device includes a housing which may be received in the oral cavity of a user, the housing enclosing electronic signal generating means and electrodes for applying a signal to neurally sensitive locations of the oral cavity to induce salivation. The device can be held in the oral cavity of the user for a period of time and be removed therefrom and to be reinserted later, or it can be fixed to the palate by clips fitted around molar teeth of the upper jaw. In its method aspect the invention involves stimulation of salivation by the application of an electrical signal to neurally sensitive locations EP 278847 relates to an apparatus for stimulating the secretion of saliva and has the form of a pellet made of a non-conductive material with electrodes on opposite faces thereof. The apparatus has no means of firm attachment within the mouth and is only held freely within the mouth and is moved from one place to another by aid of the tongue. In addition, as with the devices of Brenman et al, none of these devices can be operated by either remote or feedback control.

WO 00/44439 teaches a device and method for inducing salivation using an implanted device. Several generations of the device of the invention are envisaged including those with controllable or changeable electrical parameters, and those where changing the parameters is under the control of a salivation sensor which constantly senses mouth humidity and forms a feedback loop with the device. The invention does not however disclose how such control can be accomplished and is not enabling as to how such a salivation sensor might operate and how feedback control can be effected.

There is thus a widely recognized need for, and it would be highly advantageous to have, a system and method for electrical stimulation of salivation devoid of the above limitation.

SUMMARY OF THE INVENTION

According to one aspect of the present invention there is provided a system for electrically detecting a lack of saliva in an oral cavity of an individual and for electrically stimulating the oral cavity so as to induce production of saliva from at least one salivary gland, the system including: (a) a control device for detecting a measure of salivation in the individual and for delivering electrical impulses to the oral cavity of the individual, (b) a check device for checking a state of the control device and for modifying at least one parameter of the control device, and, (c) a computer device for exchanging information with the check device.

According to another aspect of the present invention there is provided a device for electrically detecting a measure of saliva in an oral cavity of an individual and for delivering electrical impulses to the oral cavity of the individual so as to induce production of saliva from at least one salivary gland, the device, also known as the control device, including: (a) a hermetically sealed housing adapted to be fixable within the oral cavity, (b) an electrical utility enclosed within the housing for detecting an input signal for detection of the measure of salivation and for generating the electrical impulses, the electrical utility including a power source and a signal generator, and (c) at least one pair of electrodes electrically coupled to the electrical utility, the at least one pair of electrodes adapted for contact with a tissue of the oral cavity.

According to yet another aspect of the present invention there is provided a method for electrical stimulation of salivation including the steps of: (a) attaching a device for electrically detecting a measure of saliva in an oral cavity of an individual and for delivering electrical impulses to the oral cavity of the individual so as to induce production of saliva from at least one salivary gland, the device having at least one pair of electrodes, the electrodes being placed against a tissue of the oral cavity, (b) detecting an input signal indicative of the measure of moisture within the oral cavity, (c) comparing the measure to a moisture limit value, and (d) delivering the electrical impulses based on a result of the comparing.

According to still another aspect of the present invention, there is provided a housing for an intraoral device, the intraoral device being configured so as to be fixable to at least one tooth within an oral cavity of an individual, the housing including: (a) a body and (b) an attachment element for fixing the body to the at least one tooth, wherein, the attachment element includes at least one clasp for attaching the body to the at least one tooth, the at least one clasp including at least one elastic jaw, whereby the at least one clasp fixes onto the at least one tooth by the pressure of the at least one jaw against the at least one tooth.

According to further features in preferred embodiments of the invention described below, the control device of the system includes: (1) a hermetically sealed housing adapted to be fixable within the oral cavity, (2) an electrical utility enclosed within the housing for detecting an input signal for detection of the measure of salivation and for generating the electrical impulses, the electrical utility including a power source and a signal generator, and (3) at least one pair of electrodes electrically coupled to the electrical utility, the at least one pair of electrodes adapted for contact with a tissue of the oral cavity.

According to still further features in the described preferred embodiments the power source is a battery.

According to still further features in the described preferred embodiments the battery is rechargeable, and the electrical utility includes a charge battery block for charging the battery.

According to still further features in the described preferred embodiments the electrical utility further includes a microprocessor for controlling at least one parameter of the signal generator.

According to still further features in the described preferred embodiments the microprocessor includes a memory device for storing information about the at least one parameter.

According to still further features in the described preferred embodiments the memory device is configured for storing a set of operating rules.

According to still further features in the described preferred embodiments the memory device stores a predefined and preinstalled set of the operating rules.

According to still further features in the described preferred embodiments the at least one pair of electrodes are adapted to be used for more than one function.

According to still further features in the described preferred embodiments the more than one function is selected from the group consisting of emitting the electrical impulses, receiving the input signal, exchanging information between the control device and the check device, and recharging the power supply.

According to still further features in the described preferred embodiments the housing includes an electrically conductive exterior portion, the electrically conductive portion serving as a component of the at least one pair of electrodes.

According to still further features in the described preferred embodiments the housing is adapted to be implanted within the tissue of the oral cavity.

According to still further features in the described preferred embodiments the housing includes an attachment element adapted to attach the housing to at least one tooth.

According to still further features in the described preferred embodiments the attachment element is adapted so that the housing is capable of being repeatedly attached and removed by the individual.

According to still further features in the described preferred embodiments the at least one tooth is a mandibular tooth.

According to still further features in the described preferred embodiments the at least one tooth is selected from the group consisting of a premolar tooth and a molar tooth.

According to still further features in the described preferred embodiments the attachment element is a mouth guard.

According to still further features in the described preferred embodiments the attachment element includes at least one clasp for attaching the control device to the at least one tooth, the at least one clasp including at least one elastic jaw, whereby the at least one clasp fixes onto the at least one tooth by the pressure of the at least one jaw against the at least one tooth.

According to still further features in the described preferred embodiments at least one jaw has a face, the face having an adhesion modification for increasing fixation of the at least one jaw to the at least one tooth.

According to still further features in the described preferred embodiments the face has a surface area and said adhesion modification increases the surface area of said face.

According to still further features in the described preferred embodiments the adhesion modification includes at least one groove on the face.

According to still further features in the described preferred embodiments the signal generator includes a mechanism for producing the impulses and the impulses are square-waved shaped.

According to still further features in the described preferred embodiments the signal generator includes a mechanism for producing a series of the impulses, the impulses having an intensity of between 10 and 200 microamperes, and each of the pulses lasting from 5 to 100 milliseconds.

According to still further features in the described preferred embodiments the control device is fixed in the oral cavity so as to preferably stimulate the submandibular and sublingual salivary glands.

According to still further features in the described preferred embodiments the measure of salivation is a relaxation time, the relaxation time being a measure of time required for a voltage difference between the at least one pair of electrodes to reach a predetermined level of an initial value of the voltage difference after a measuring pulse is applied.

According to still further features in the described preferred embodiments the predetermined level is selected from the group consisting of 40% and 50%.

According to still further features in the described preferred embodiments steps (b) through (d) of the method for electrical stimulation of salivation are repeated iteratively.

According to still further features in the described preferred embodiments the method further includes the step of modifying a parameter of the device.

The present invention successfully addresses the shortcomings of the presently known configurations by providing a system and method for electrical stimulation of salivation that can be used for the treatment of xerostomia that can be used to electrically detect a lack of saliva in the oral cavity and for electrically stimulating the oral cavity so as to induce the production of saliva from the salivary glands. The principal advantage of the present invention over the prior art is that the system according to the present invention is constructed and designed so that the system can electrically detect a lack of saliva, the parameters of the electrical stimulation can be controlled, and the parameters can be controlled under feedback control using the electrical detection of saliva quantity.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
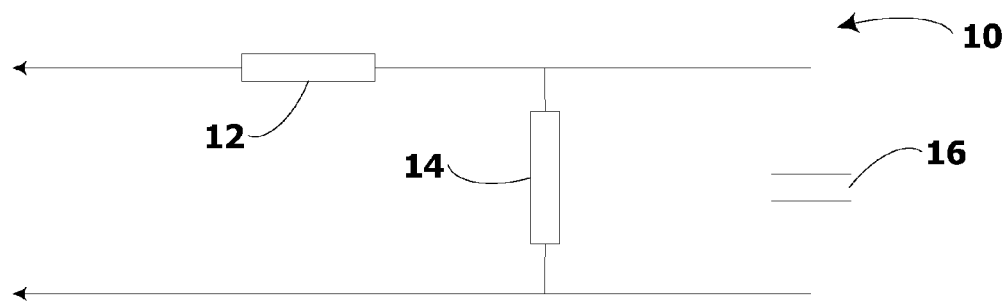
FIG. 1 is a schematic diagram of a physical model of the salivary glands.

The present invention is of a system and method for electrical stimulation of salivation that can be used for the treatment of xerostomia. Specifically, the present invention can be used to electrically detect a lack of saliva in the oral cavity and for electrically stimulating the oral cavity so as to induce the production of saliva from the salivary glands. The principal advantage of the present invention over the prior art is that the system according to the present invention is constructed and designed so that the system can electrically detect a lack of saliva, the parameters of the electrical stimulation can be controlled, and the parameters can be controlled under feedback control using the electrical detection of saliva quantity.

The principles and operation of a system and method for electrical stimulation of salivation according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
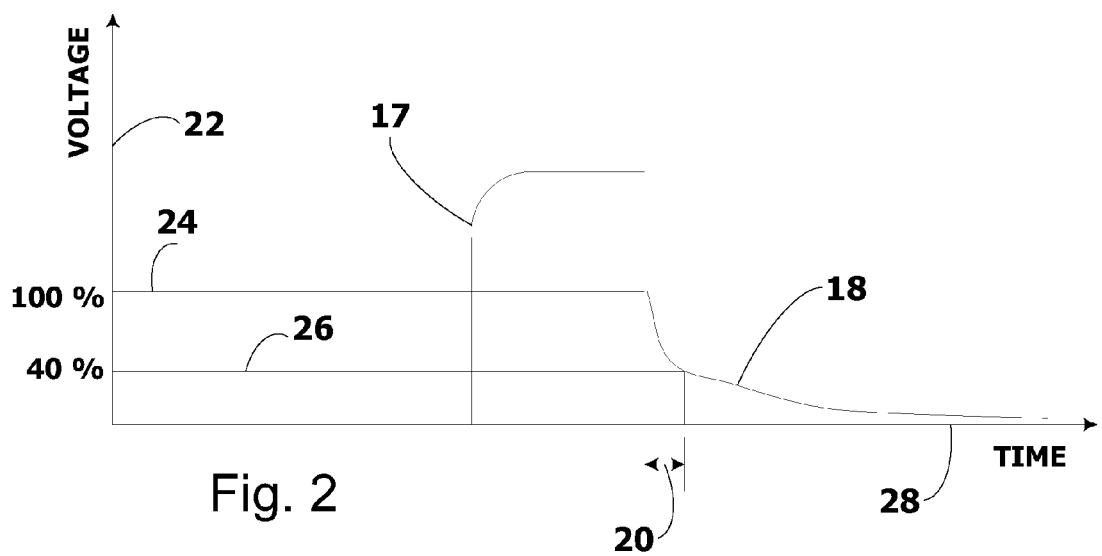
FIG. 2 is a graph of measured electrical activity returned after a stimulatory pulse is applied to the circuit of FIG. 1.

Referring now to the drawings, FIG. 1 is a schematic diagram of a physical model of the salivary glands. According this model, the salivary glands can be described as an electrical circuit (10) with an input resistor R1 (12) connected to a parallel resistor R2 (14) and capacitor C (16). When a current pulse is applied to circuit 10, a current reply is returned. The resulting reply is measured and defines a curve (18) as illustrated in FIG. 2. From curve 18, various parameters are estimated including resistance, capacity and the time for the circuit to discharge the circuit's capacity following the pulse. The discharge time is the time required by the circuit to return to its baseline activity after receiving a stimulation pulse.

For purposes of this specification and the accompanying claims, the term "relaxation time" [20] refers to, and is defined as, the time (28) required for a measured voltage difference (22) to reach a predetermined level, preferably 40% (26), or 50% in some embodiments, of its initial value (24), after a measuring pulse (17) is applied.

Based on this model, as further described hereinbelow in greater detail, an electrical pulse is administered to the salivary glands and then following a short pause (several seconds) the voltage difference between the two electrodes is measured. These measurements are used to determine the relaxation time 20 of the gland. Results of experimental investigation, detailed herein below under "Examples", have demonstrated a good correlation between the relaxation time 20 of the gland and glandular activity, the glandular activity being defined as the quantity of saliva present.

Figure 3:
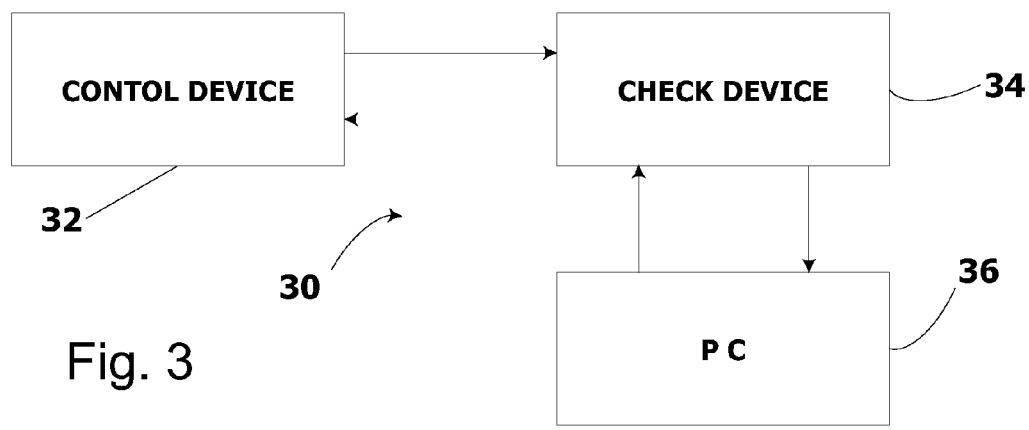
FIG. 3 is a functional block diagram of a preferred embodiment of the system for electrical stimulation of salivation of the present invention.

FIG. 3 shows a functional block diagram of a preferred embodiment of the system for electrical stimulation of salivation of the present invention, the system generally designated 30. As illustrated in FIG. 3, system 30 comprises 3 parts: a control device 32, a check device 34 and a computer device 36. Control device 32 functions to emit pulses to at least one salivary gland in the mouth of an individual. Check device 34 functions to check the state of control device 32, to install, change, modify and delete the stimulation pulse parameters of control device 32 and to exchange information with computer device 36. The exchange of information between check device 34 and computer device 36 includes transmission of data from control device 32 to computer device 36 and reception of stimulation pulse parameters from computer device 36 to be transferred to control device 32. This configuration of system 30 gives to the doctor who is the operator of system 30 the full picture about the treatment of the patient, including the possibility of analyzing the state of the patient (e.g., relaxation time, parameters of treatment, correlation of relaxation time with the pulse parameters) and changing the stimulation pulse parameters, including quantity and time parameters.

Figure 4:
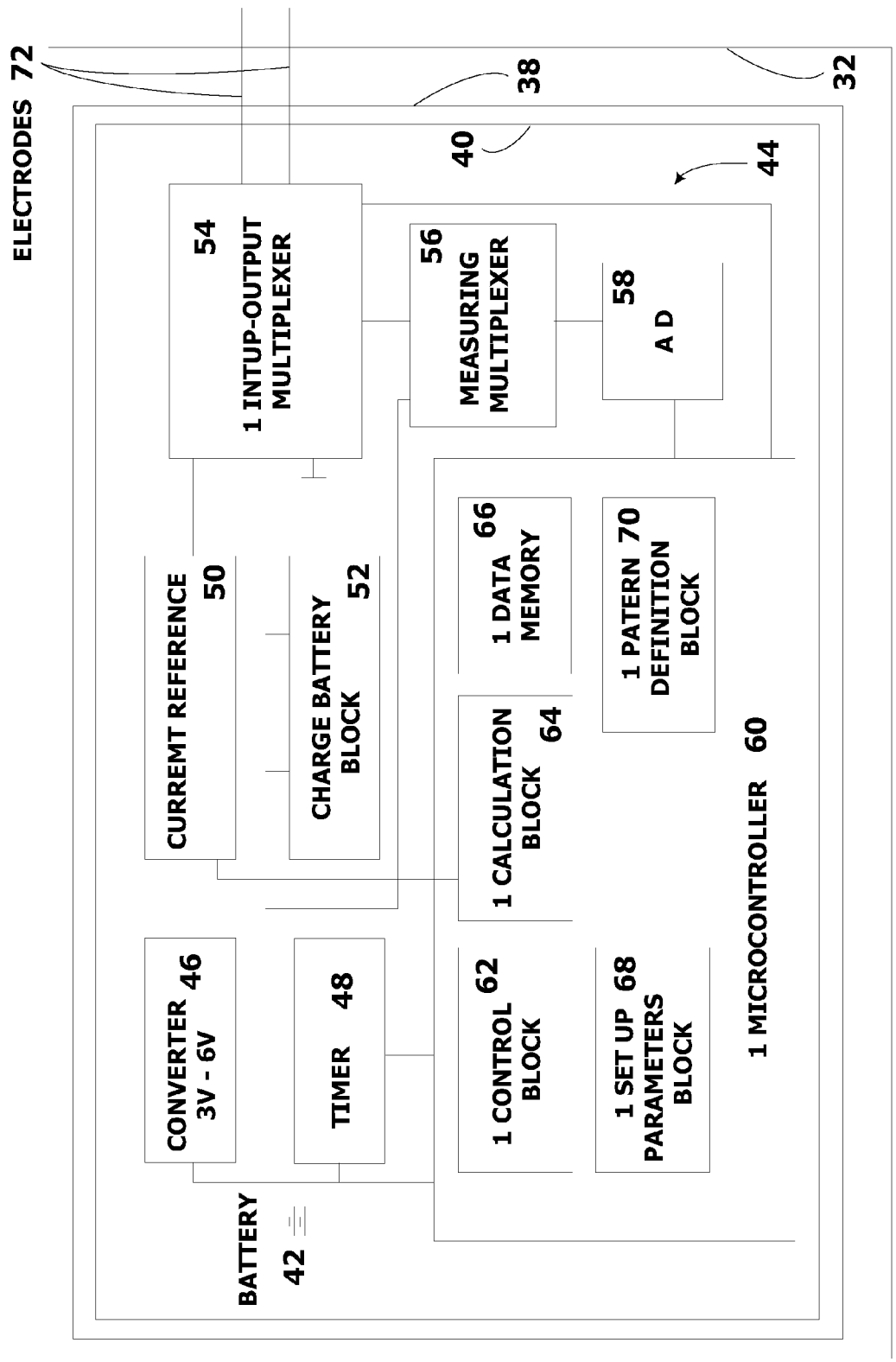
FIG. 4 is a functional block diagram showing the major components and connections of a control device of the system according to the present invention.

FIG. 4 illustrates the components of control device 32 in greater detail. Control device 32 has a hermetically sealed housing 38 encasing an electric utility generally designated 40. In certain preferred embodiments of the present invention, housing 38 is adapted to be attached to at least one tooth and in other preferred embodiments housing 38 is adapted to be permanently implanted within tissues of the oral cavity. Electric utility 40 comprises a battery 42 and an electronic circuitry 44. Battery 42 is preferably a miniature battery supplying low voltage (preferably between 3-5 volts, most preferably 3 volts) and can be of a perishable type or can be of a rechargeable type. Electronic circuitry 44 preferably includes the following components: a converter 46, a timer 48, a current reference 50, a charge battery block 52, a first input-output multiplexer 54, a measuring multiplexer 56, an analog-digital converter 58, and a first microcontroller 60, with operative associations, signal flow, and electrical couplings as indicated in FIG. 4. First microcontroller 60 is further divided into subunit blocks as illustrated in FIG. 4 including: a first control block 62, a first calculation block 64, a first data memory 66, a first set-up parameters block 68 and a first pattern definition block 70. First data memory 66 includes a writeable memory device such as, but not limited to, ROM, RAM, PROM, EPROM, EEPROM, flash memory etc. Blocks 62, 64, 68, and 70 are each program modules, performing the respective processor functions described in their titles. First input-output multiplexer 54 is operatively associated with and electrically connected to at least one pair of electrodes 72. At times housing 38 may be provided with an electrically conducting exterior covering the whole or part of the surface of housing 38, in which case the electrically conducting portion of the housing may serve as one of the electrodes 72 of device 32. When housing 38 serves as one of the electrodes 72 it is insulated. Preferably device 32 contains only one pair of bi-directional, multi-functional electrodes 72. This one pair of bi-directional, multi-functional electrodes 72 functions to emit stimulatory pulses, receive returning electrical signals, receive current for charging battery 42, and for communication with check device 34 to exchange information between control device 32 and check device 34. Alternatively device 32 may be provided with independent electrode pair assemblies for separate functions or alternatively one electrode may be shared by more than one functional component and the other electrode may be separate for each functional component. Electrodes 72 are preferably insulated from housing 38 and have exposed conducting ends. The exposed conducting ends are placed in the vicinity of either a nerve innervating a salivary gland or in the vicinity of a gland itself as is further described hereinbelow.

All the functional blocks may either be individual microprocessors or other CPU's or control programs for a multiple-use processor. They may include a factory-set group of default rules.

Converter 46 converts low voltage supplied from battery 42 to high voltage for supplying current reference 50, from 3v to 6v, as a non-limiting example. Timer 48 provides time pulses to first microcontroller 60. Current reference 50 serves as a signal generator to supply stimulation pulses of electrical current with parameters under the control of first microcontroller 60. Charge battery block 52 is present only in those preferred embodiments that contain a rechargeable battery as battery 42 and is used to apply a charge to rechargeable battery 42. First input-output multiplexer 54, is connected to current reference 50, charge battery block 52, first microcontroller 60, and measuring multiplexer 56 with operative associations and signal flow as indicated in FIG. 4, as well as to the at least one pair of electrodes 72. First input-output multiplexer 54 performs the following functions: emit stimulatory pulses via electrodes 72 to salivary gland, measure electrical activity state of salivary gland, charge battery, (in which case multiplexer 54 receives current and transfers the current to charge battery block 52), transmit information to check device 34 and receive information from check device 34. Measuring multiplexer 56 can switch between measuring the voltage output of the battery, for checking battery condition (and determining whether battery needs to be charged or changed), and measuring electrode voltage for determining the electrode contact quality and for determining relaxation time. Analog-digital converter 58 converts analog information into digital code for processing by first microcontroller 60. First microcontroller 60 performs all of the calculation and data processing functions of device 32 as described herein. Additional components such as, but not limited to, contacts and wires, may be required to establish the connections as described hereinabove. One of ordinary skills in the art would know how to operatively assemble these components.

Figure 11:
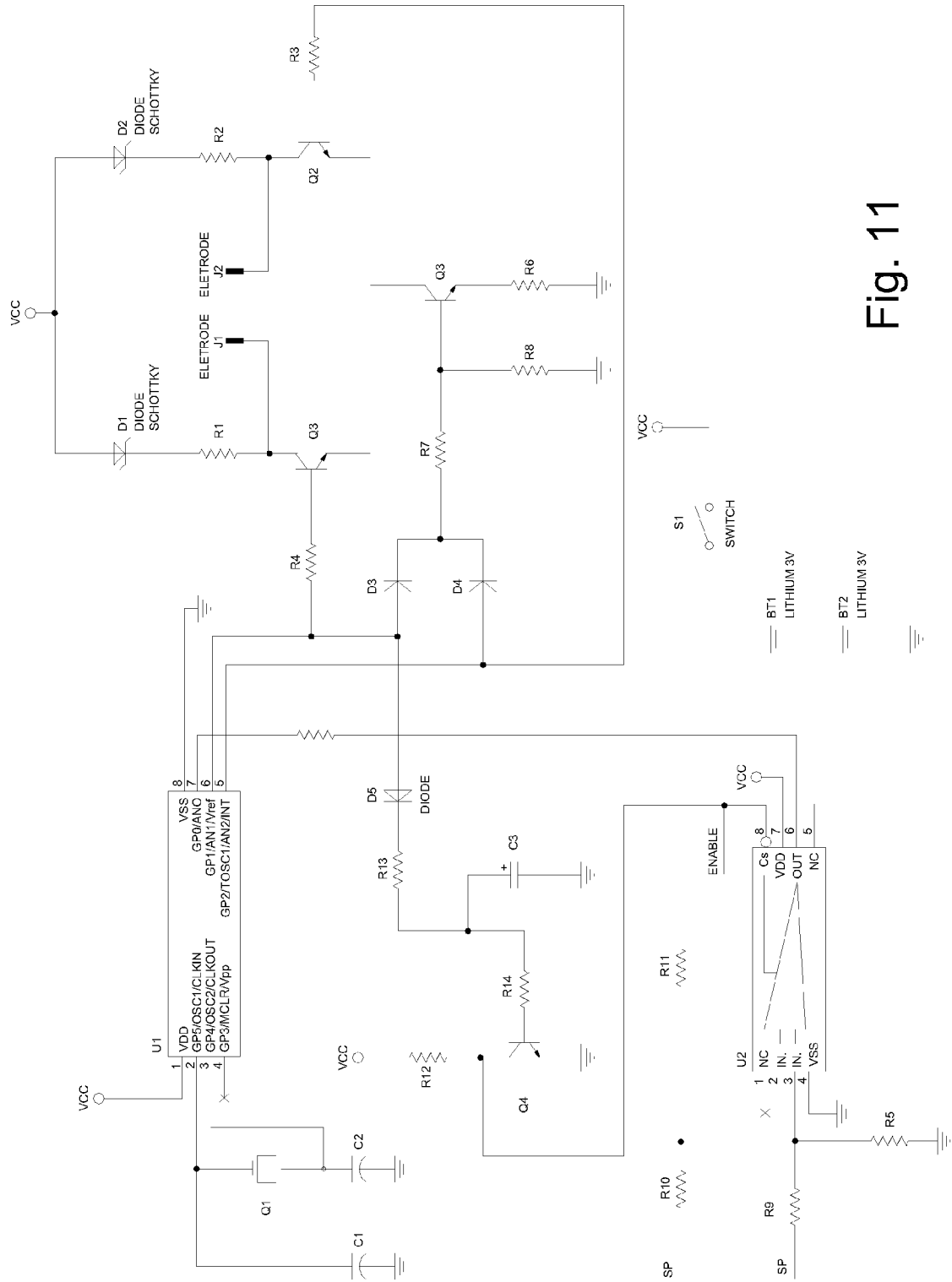
FIG. 11 is a schematic circuit diagram illustrating aspects of the circuitry according to the present invention; and, FIGS. 12-14 illustrate alternate examples of methods of operation of the present invention.

FIG. 11 is an a schematic circuit diagram illustrating a non-limiting example of a preferred embodiment of a circuit corresponding to features of control device 32 as illustrated in the block diagram, FIG. 4. Such a circuit as illustrated (as a non-limiting example) in FIG. 11 is capable of being fabricated as a two level circuit, 0.2 mm thick and 16 mm in diameter, using SMD packing, with a 3V lithium battery (e.g. 42) mounted on top, capable of being placed in housing (e.g. 38) of appropriate size for fixation in the oral cavity.

Figure 5:
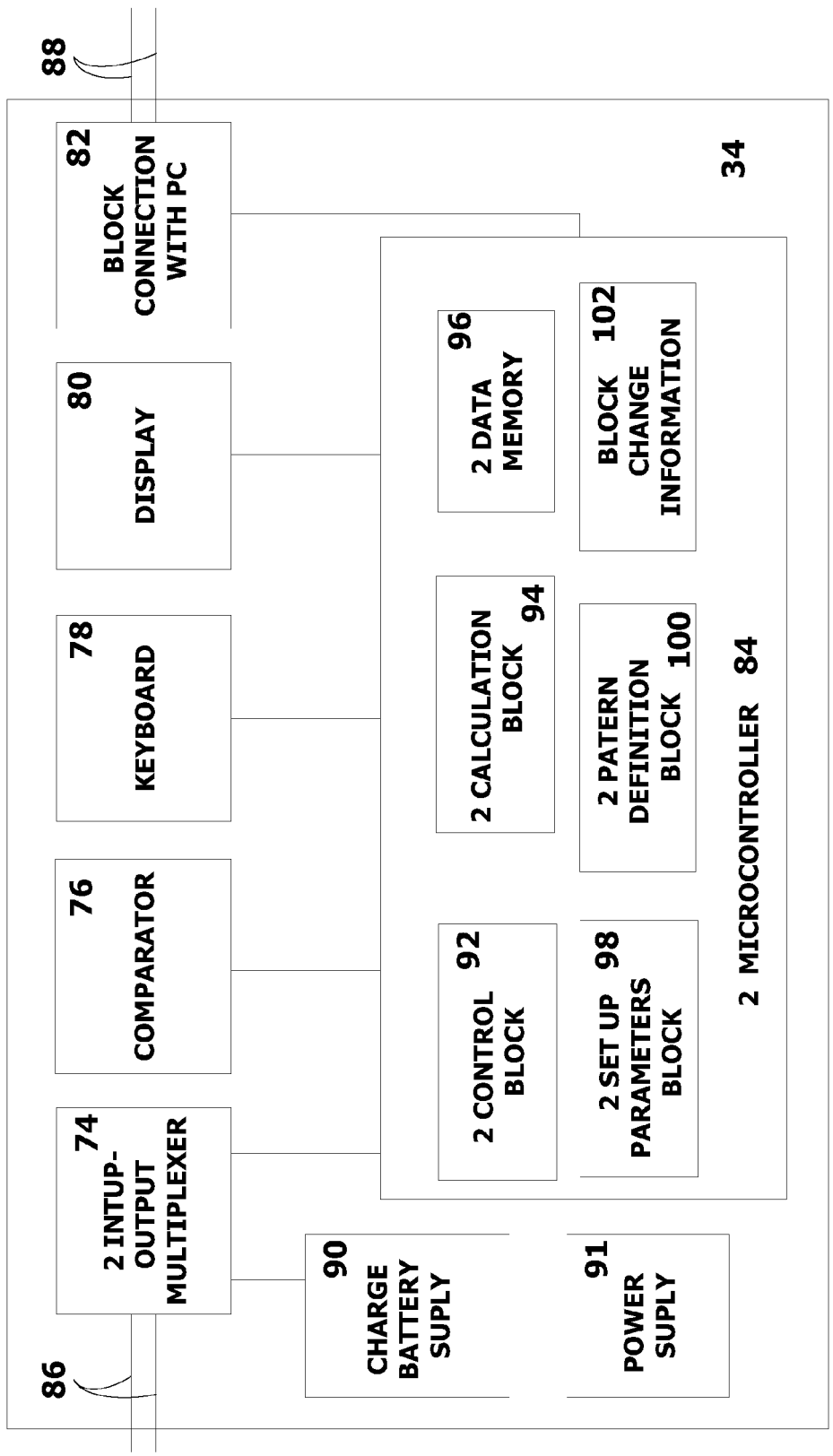
FIG. 5 is a functional block diagram showing the major components and connections of a check device of the system according to the present invention.

The components and connections of check device 34 are illustrated in greater detail in FIG. 5. check device 34 preferably includes a second input-output multiplexer 74, a comparator 76, a keyboard 78, a display 80, a PC block connection 82, a second microcontroller 84, a charge battery supply 90, and a power supply 91. The operative associations, signal flow, and electrical couplings between the components of check device 34 are preferably as indicated in FIG. 5. Second input-output multiplexer 74 is operatively associated with at least one pair of input-output connections 86 which serve to facilitate communication between check device 34 and control device 32. Second input-output multiplexer 74 performs the following functions: transmits information to control device 32, receives information from control device 32 and charges battery 42. Comparator 76 checks the signal from control device 32. Information to be installed in system 30 may be introduced (input) into check device 34 via keyboard 78 as is known in the art. Data is visually presented to the operator by display 80. Non-limiting examples of display 80 are conventional computer monitors, cathode ray tube display screens, liquid crystal displays and light emitting diodes. PC block connection 82 executes the communication between check device 34 and computer device 36 via at least one communication channel 88. Communication channel 88 utilizes any means of data transfer including, but not limited to, data transfer by a direct cable, connection, a telephone connection, a cellular phone connection, an Internet connection, an infrared frequency connection, a local area network connection, and a radio frequency connection. Also specifically envisaged as being encompassed by communication channel 88 is data transfer through transfer of tangible media containing data between devices 34 and 36. Such tangible media includes, but is not limited to, media such as computer diskettes, CD ROM discs, magneto-optical cartridges, ZIP discs, and any other physical entity bearing digitally encoded data.

Depending upon the exact nature of such configurations, additional components, for example wires, antennas, receivers, transmitters and/or transceivers, a telephony network and other equipment may be required for communication. A portion of these additional components may already exist as part of established communication networks. One ordinarily skilled in the art will be capable of assembling such a communication channel 88 from commercially available components.

Charge battery supply 90 is employed in those preferred embodiments of control device 32 which include a rechargeable battery 42. It serves to apply a charge to battery 42 through charge battery block 52. Power for this purpose and all other functions of device 34 comes from power supply 91. Second microprocessor 84 performs all of the intelligence and data processing functions of check device 34 and preferably includes subunit program module blocks as illustrated in FIG. 5 including: a second control block 92, a second calculation block 94, a second set-up parameters block 98, a second pattern definition block 100, and a change information block 102, as well as a second data memory 96.

Computer device 36 indicates any type of electronic device which is capable of performing computations, including, but not limited to, personal computers (PC); Macintosh™ computers; mainframe computers; graphical workstations; handheld computing devices; or any other known and available computational device.

Control device 32 is fixed in the mouth of a patient either for a short term or long term. In certain embodiments of the present invention device 32 is not fixed and is held freely in the mouth and in other embodiments control device 32 is preferably removable by the patient. For the purposes of this specification and the accompanying claims "long-term" is meant to refer to a prolonged time period of several weeks to several months or preferably several years. For the purposes of this specification and the accompanying claims "short-term" is meant to refer to a shorter time period of several hours to a day or several days.

Figure 6A:
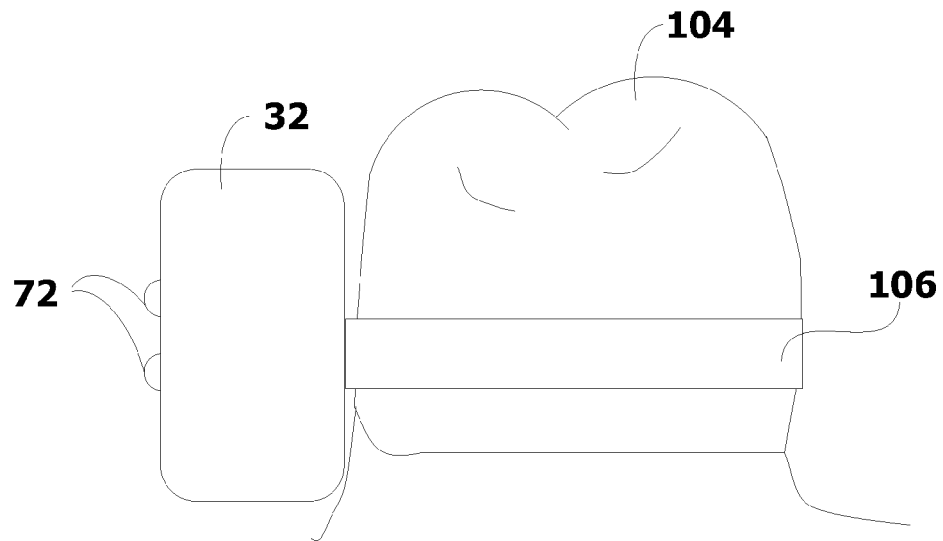
FIG. 6A shows the control device of the system according to the present invention attached to a tooth.
Figure 6B:
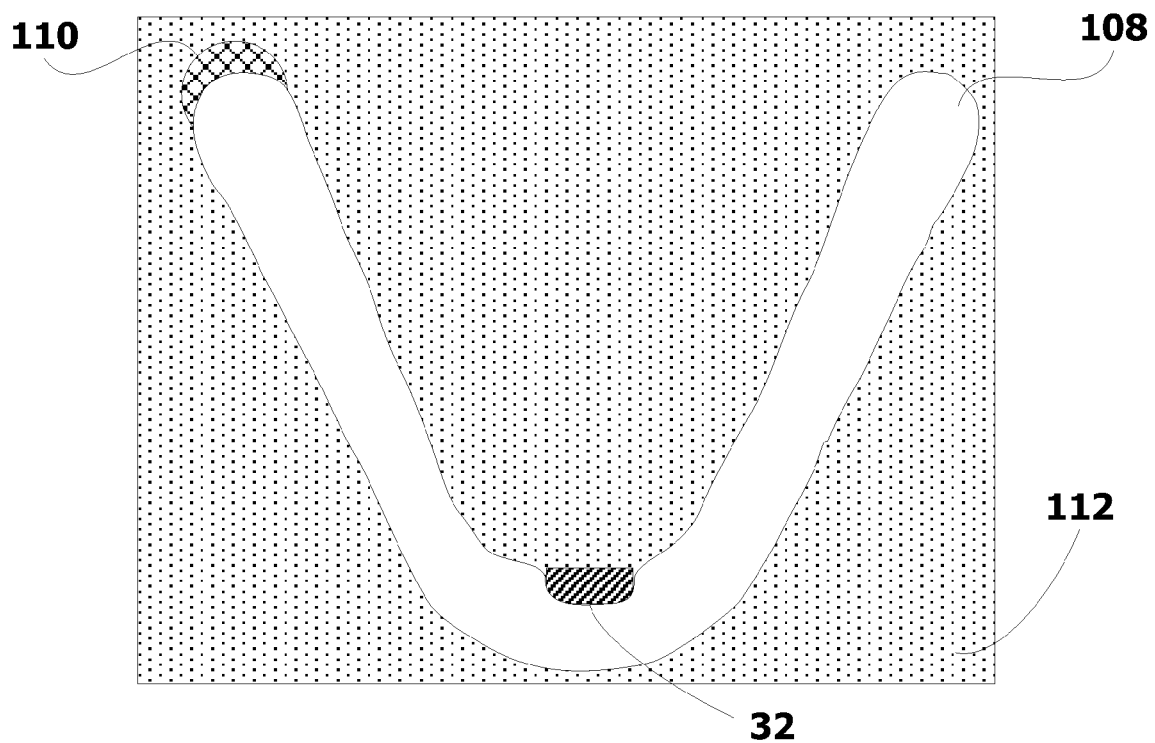
FIG. 6B shows the control device of the system according to the present invention attached to the mandibular teeth by a mouth guard.

FIG. 6A shows control device 32 attached to a molar tooth 104 by means of a band 106, which may take the form for example, but not limited to, an orthodontic band, orthodontic braces, a dental fixture, a hooking arrangement or other such physical structure as to affix the device to the teeth or other oral structure as my be known in the art. In certain embodiments device 32 is fixed in the oral cavity so as to preferably stimulate the submandibular and sublingual glands. One such embodiment is illustrated in FIG. 6B. FIG. 6B illustrates fixation of control device 32 on the mandibular teeth 110 through use of a mouth guard 108. Mouth guard 108 is a flexible plastic frame covering the lower teeth. Mouth guard 108 is a fixture, resembling an athletic mouth guard, also commonly used in dental treatment, usually worn at night, especially after orthodontic dental alignment, or for treatment of bruxism. This attachment is made so as to place the electrodes in the sublingual area 112 as a non-limiting example. In other embodiments, device 32 may be implanted within tissues with the mouth such as the gums, teeth, jaw bones, palate, sublingual tissues, buccal mucosa and the like.

Figure 10A:
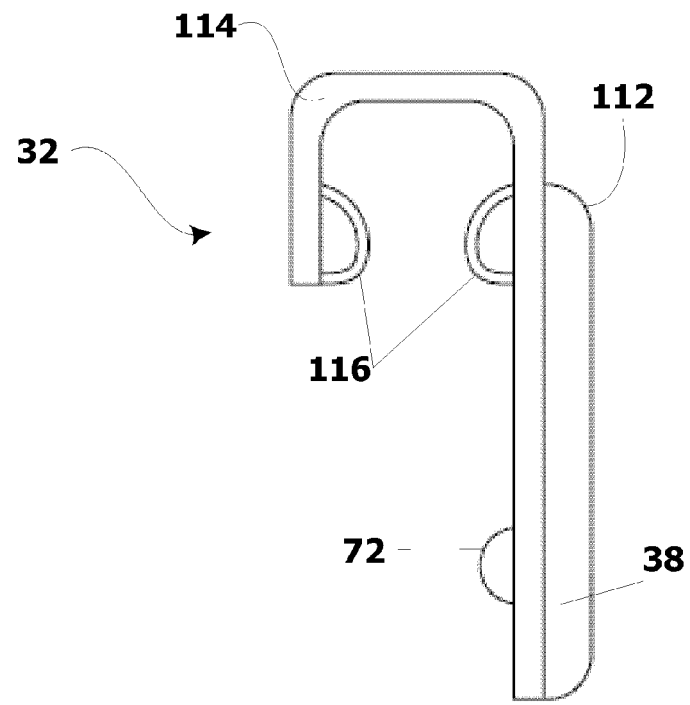
FIG. 10A is a side view illustrating a preferred embodiment of the housing of the control device of the system according to the present invention.
Figure 10B:
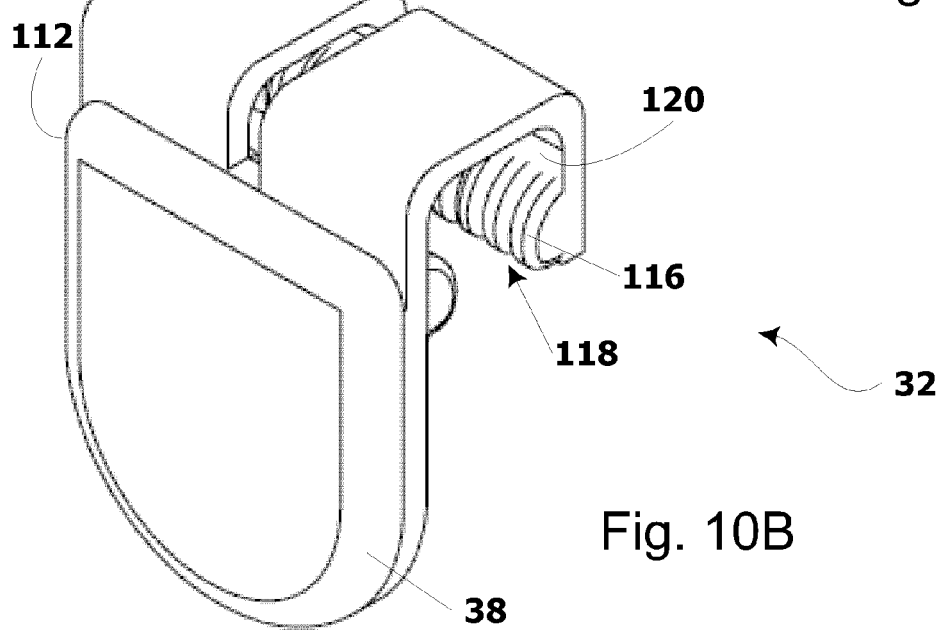
FIG. 10B is a perspective view illustrating a preferred embodiment of the housing of the control device of the system according to the present invention.

FIG. 10a illustrates an alternative preferred embodiment for fixation of control device 32 within the oral cavity. FIG. 10 shows housing 38 being adapted to include at least one clasp 114 for attaching control device 32 to at least one tooth. According to the preferred embodiment as illustrated in FIG. 10b, control device 32 does not have to be individually fabricated for a specific patient but rather device 32 is fabricated in a specific limited range of sizes, suitable for use in patients with different size and shapes of oral structures. Housing 38 is fabricated from a biocompatible material and seals and encases (within a body 122 of housing 38), electric utility 40 which includes battery 42 and electronic circuitry 44 as well as at least one pair of electrodes 72. At least one clasp 114 is fabricated for example from an elastomeric substance, such as a flexible acrylic or other plastic, or a metal, as non-limiting examples, so as to fix onto at least one tooth preferably by an elastic, spring recoil, clamping action. Clasp 114 fixes onto the at least one tooth by the pressure and friction of at least one jaw 116 of elastic spring clasp 114 against the at least one tooth (and associated oral structures, such as the gum) to which clasp 114 is applied. In configurations such as that illustrated in FIG. 10b, with more than one jaw 116, different jaws may have different degrees of elasticity, with one of the at least one jaws 116 being more elastic and one being more rigid. The face 120 of jaw 116 in some configurations is fitted with at least one groove 118 for conforming to indentations on the surface of the at least one tooth to which device 32 is applied. These modifications of face 120 are done so as to increase the surface area of contact between face 120 and the oral structures to which device 32 is fixed so as to increase the friction between the at least one jaw 116 and the oral structure to which device 32 is attached. The modifications of face 120 increase the adhesion and fixation of device 32 in the oral cavity. In other embodiments, other modifications of face 120 are employed to increase the surface area or the friction, such as finger-like or tentacle-like projections, or suction cups. Still other modifications are employed to otherwise enhance fixation such as the placement of magnets and magnetically susceptible material in clasp 114. In applying control device 32 to the at least one tooth a lubricant substance can be applied or in some circumstances a temporary adhesive substance (similar to denture fixative) can be applied to assist in holding clasp 114 on the at least one tooth. Clasp 114 has sufficient flexibility as to be conformable to different sizes and shapes of tooth. It can be configured so as to be slidable from one tooth to another. Clasp 114 and housing 38 may be used on a mandibular or maxillary tooth, on either the right or left side of the oral cavity, and on a front or rear tooth. Preferably clasp 114 and housing 38 are adapted to fix device 32 onto at least one mandibular premolar or molar tooth placing electrodes 72 against the mucosal surfaces of oral structures of the lower jaw. Housing 38 is configured so as to insure contact of electrodes 72 with the oral tissues. Device 32 as illustrated in FIG. 10 can thus be easily attached and released and is suitable for use for short periods of time (for example 4 to 8 hours at a time, daily) or longer and can be made so as to be easily cleanable, and used, for example, for two to three months before being replaced. Such a housing 38 with an attachment member such as clasp 114 may find use in other intraoral devices used for diagnostic and treatment purposes. Where more than one intraoral device is used at a time, the housings of the devices may be connected to one another by a connecting member such as band or elastic. For example a band may connect two such housings on different sides of the mouth, or an elastic may be employed to connect two housings, one on the mandibular teeth and one on the maxillary teeth.

The stimulation sequence delivered by control device 32 typically involves emitting of a series of square wave shaped current pulses. Typically, the pulse has an intensity within the range of 10-200 microamperes, preferably 60-120, most preferably 100 with each pulse lasting about 5-100 millisecs, preferably 10-30, most preferably 10-20 msec, with a pause between pulses of 50-1000 ms, preferably 100-500 ms, most preferably 400-600 ms. Each pulse may be either single or dual-phase polarity, preferably dual-phase polarity. The pulse numbers in each series may be from 60-600, preferably 100-400, and most preferably 200-300.

Each parameter may be set prior to use or use the pre-set default parameters. After, installation, some parameters may be set for the individual particularly the set moisture level which is determined by relaxation time. The electronic circuitry by which stimulating signals can be produced and applied in the mouth according to the present invention is well described in the art (see, for example, U.S. Pat. Nos. 4,519,400, 4,637,405, 4,244,373, and 5,188,104). It will be appreciated that other specific circuitry capable of performing the same function may occur to those skilled in the art.

Figure 7:
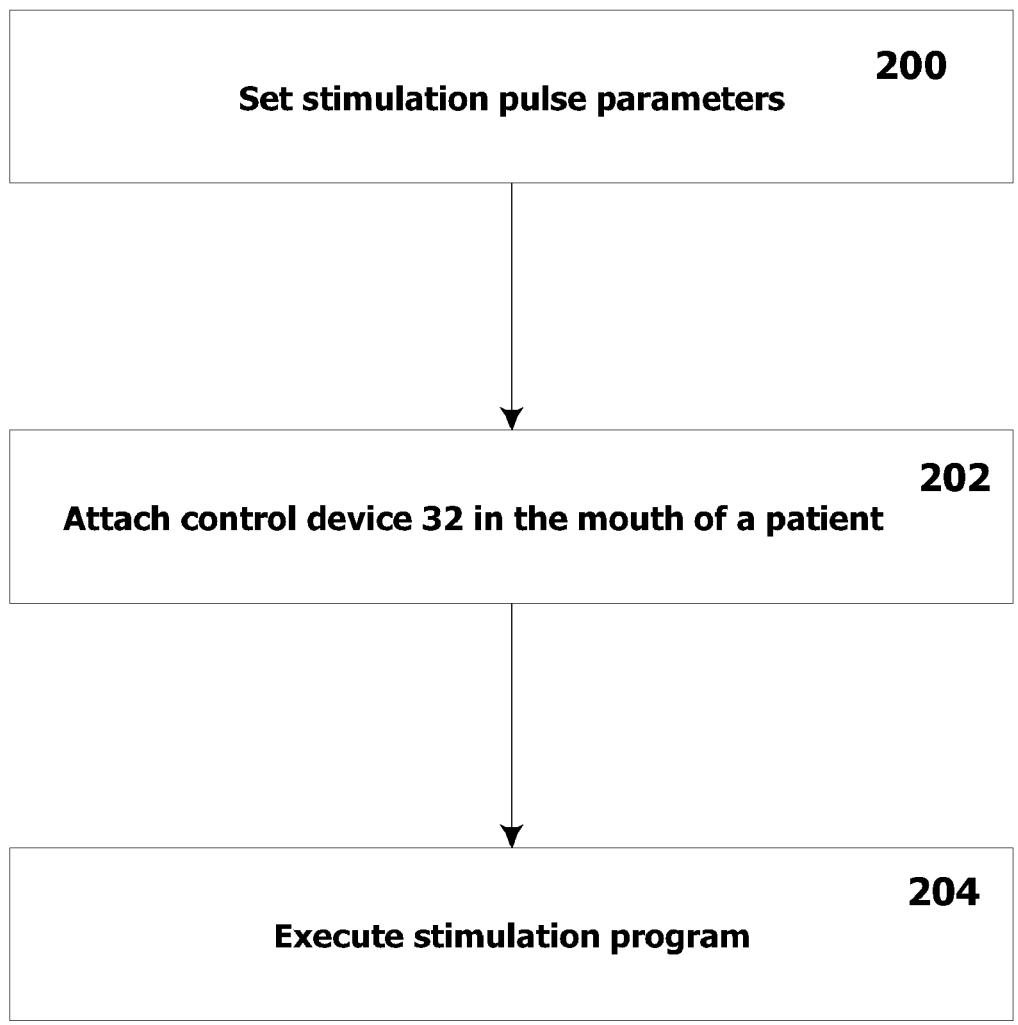
FIG. 7 is an illustrative flowchart for the purpose of understanding the method according to the present invention.

The above described system for electrical stimulation of salivation will find use primarily in conjunction with a method for electrical stimulation of salivation that can be used for the treatment of xerostomia. Such a method for electrical stimulation of salivation includes the steps of: (a) attaching a device for electrically detecting a measure of saliva in an oral cavity of an individual and for delivering electrical impulses to the oral cavity of the individual so as to induce production of saliva from at least one salivary gland (such as control device 32), device 32 having at least one pair of electrodes (72) being placed against a tissue of the oral cavity; (b) detecting an input signal indicative of the measure of moisture within the oral cavity; (c) comparing the measure to a moisture limit value; and (d) delivering the electrical impulses based on a result of the comparing. This method for use of system 30 to treat xerostomia may be best understood with reference to FIG. 7. The method for electrical stimulation of salivation making use of system 30 as disclosed hereinabove includes, as a non-limiting example, the steps of: (a) step 200: setting stimulation pulse parameters. The doctor can accept the pre-set default parameters of system 30 or can change the default parameters and install a new set of parameters. This action is performed using control device 34, and preferably computer device 36. (b) Step 202: attaching control device 32 in the mouth of a patient, with the electrodes thereof in close proximity to the salivary glands. (c) Step 204: Executing stimulation program 206.

Figure 8:
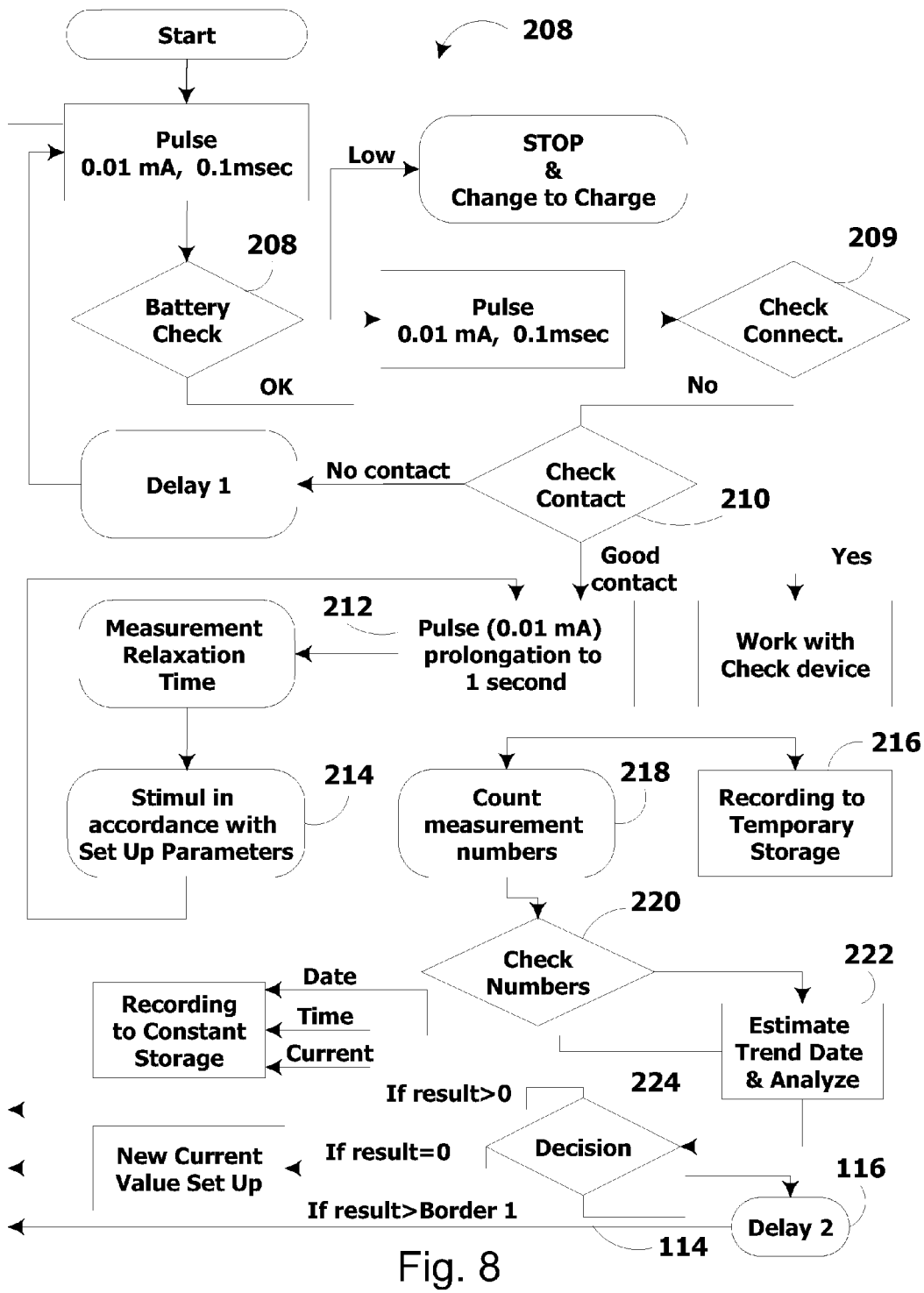
FIG. 8 is an illustrative flowchart in greater detail for the purpose of understanding the method according to the present invention.

The further steps of stimulation program 206 are illustrated in the flow chart of FIG. 8. The method of stimulation program 206 further comprises the steps of: (1) 208: Checking battery quality. If battery quality is good, proceed to step 209, if not change or charge battery. (2) 209: Checking for connection of control device 32 with check device 34. If connected, exchange information between devices 32 and 34. If no connection, proceed to: (3) 210: Checking contact quality. If no contact, return to 208. (4) 212: Emitting a measuring pulse and measuring parameters of the state of the salivary gland (e.g., resistance, capacity, relaxation time). (5) 214: Emitting a salivation inducing series of pulses in accordance with set-up parameters. (6) 216: Recording parameters to temporary memory. (7) 218: Counting number of pulses (8) 220: Repeating from step 206 until the number of pulses equals the installed parameter of number of pulses to deliver (9) 222: Estimating trend data and analyze. (224) Deciding on emitting further pulses. If trend derivative >0, continue with emitting pulses by returning to step 208. If trend derivative is =0, set up new parameters. This may be performed, as a non-limiting example, by microprocessor 46, where control block 62 interacts with current reference 50 to change the current level (e.g., from 50 to 150 microamperes as a non-limiting example) or changes the cycle timing parameters (e.g., changing the timing of the pulse emission or pause time as non-limiting examples.) If trend derivative>a border 1 (114) (which can be either a pre-set, or entered parameter, such as a 1 second relaxation time difference between measurements as a non-limiting example), stop emitting pulses and after delay 2 [116] (which can be either a pre-set, or entered parameter, such as 5-30 minutes as a non-limiting example), return to step 208. The flow chart of FIG. 8 shows these steps in somewhat greater detail.

Figure 12:
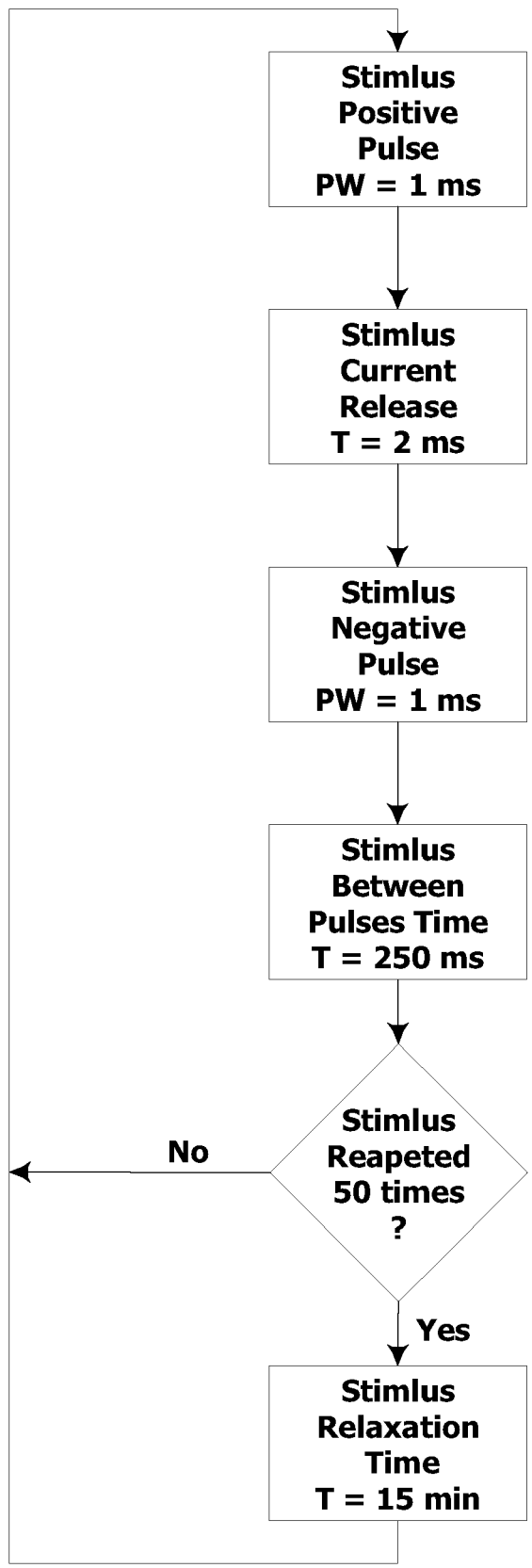
Figure 13:
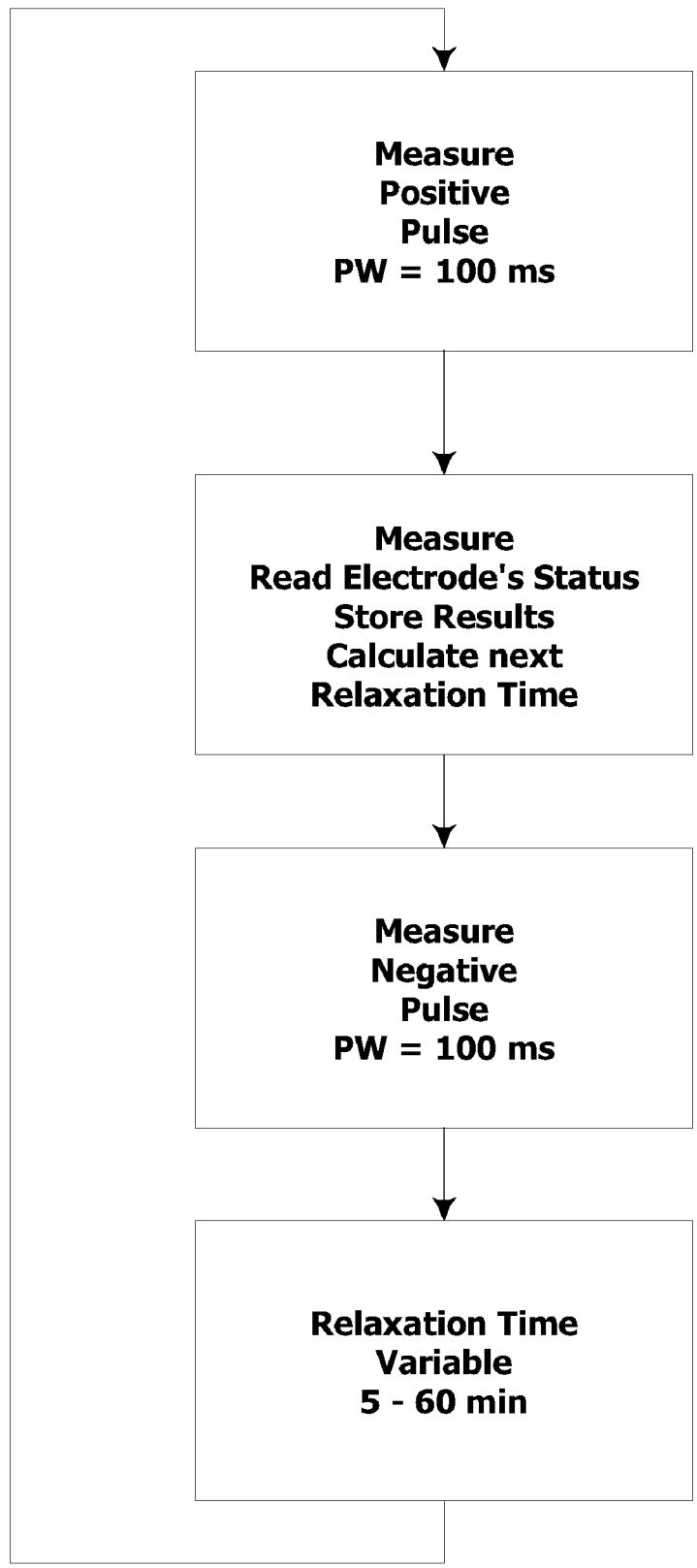
Figure 14:
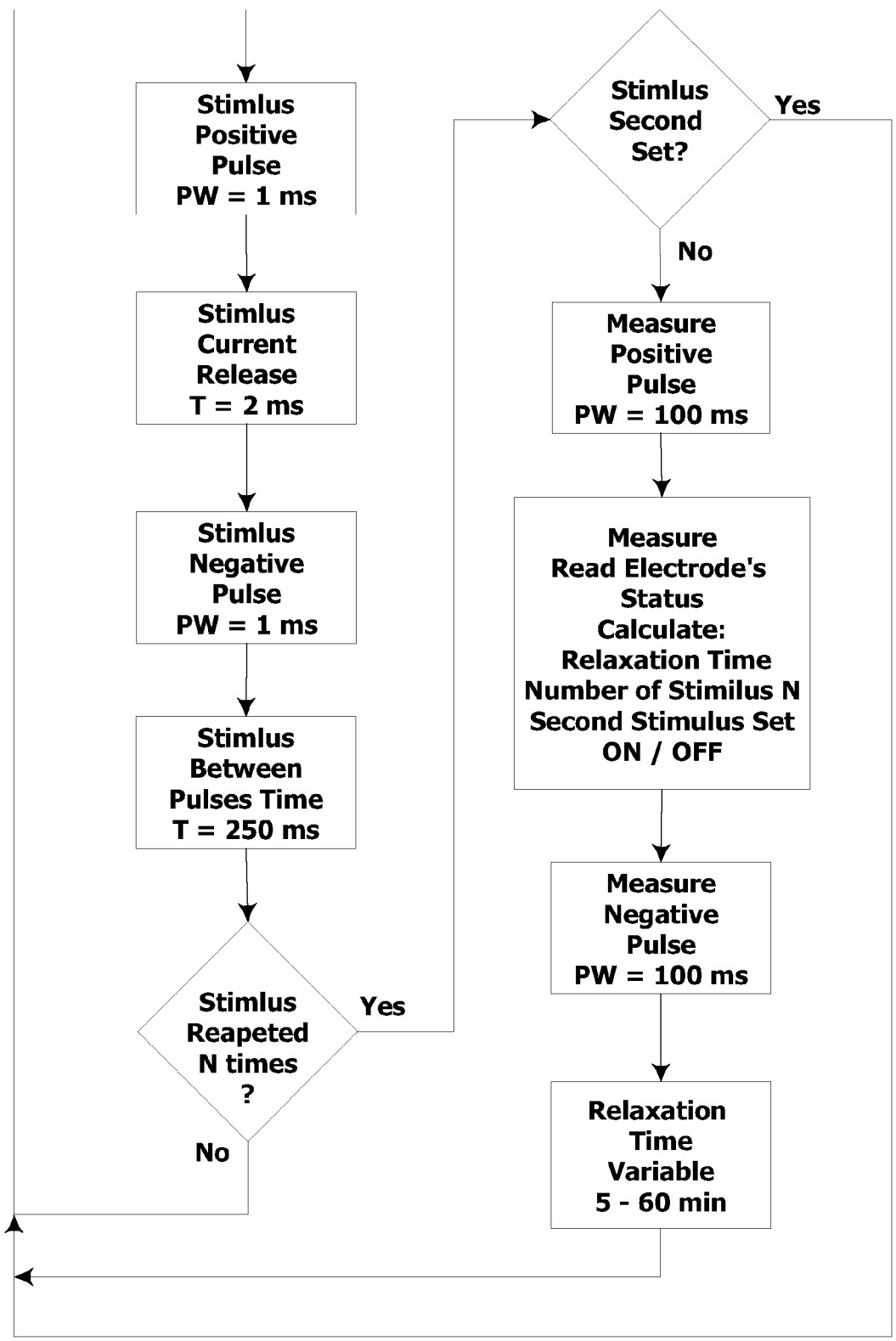

The flow charts of FIG. 12-14 illustrate alternate algorithms as non-limiting examples of methods of use of control device 32 and system 30 for delivering a stimulus only (FIG. 12), measuring only (FIG. 13), and stimulus and measuring (FIG. 14). The algorithm of FIG. 14 is capable of incorporating adaptation and "learning".

Further specifically envisaged as being within the scope of the present invention are alternate applications of this system and method for electrical stimulation of secretion of other body tissues, such as other exocrine glands—for example, but limited to, the lacrimal gland, which is also involved in other sicca syndromes such as Sjogren's syndrome (presenting with dry eyes), or the mammary gland. Also specifically envisaged as being within the scope of the present invention are alternate applications of this system and method in non-human species.

The present invention successfully addresses the shortcomings of the presently known configurations by providing a system and a method of using same for electrically detecting a lack of saliva in the oral cavity and for electrically stimulating the oral cavity so as to induce the production of saliva from the salivary glands.

Additional objects, advantages, and novel features of the present invention will become apparent to one ordinarily skilled in the art upon examination of the example hereinbelow, which is not intended to be limiting. Additionally, each of the various embodiments and aspects of the present invention as delineated hereinabove and as claimed in the claims section below finds experimental support in the example described hereinbelow.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

EXAMPLE

Reference is now made to the following example, which together with the above descriptions, illustrate the invention in a non limiting fashion.

Preliminary tests have been conducted to test the relation between relaxation time, as defined hereinabove, and "mouth moisture." Saliva was measured by standard "whole saliva" procedures. The steps of the experiment were as follows: (1) Measure relaxation time, (2) Measure whole saliva (3 minutes), (3) Administer stimulus for 5 minutes to increase salivation (60 µA, 100 µA, 300 µA, 500 µA), (4) Measure whole saliva (3 minutes), and (5) Measure relaxation time.

Figure 9A:
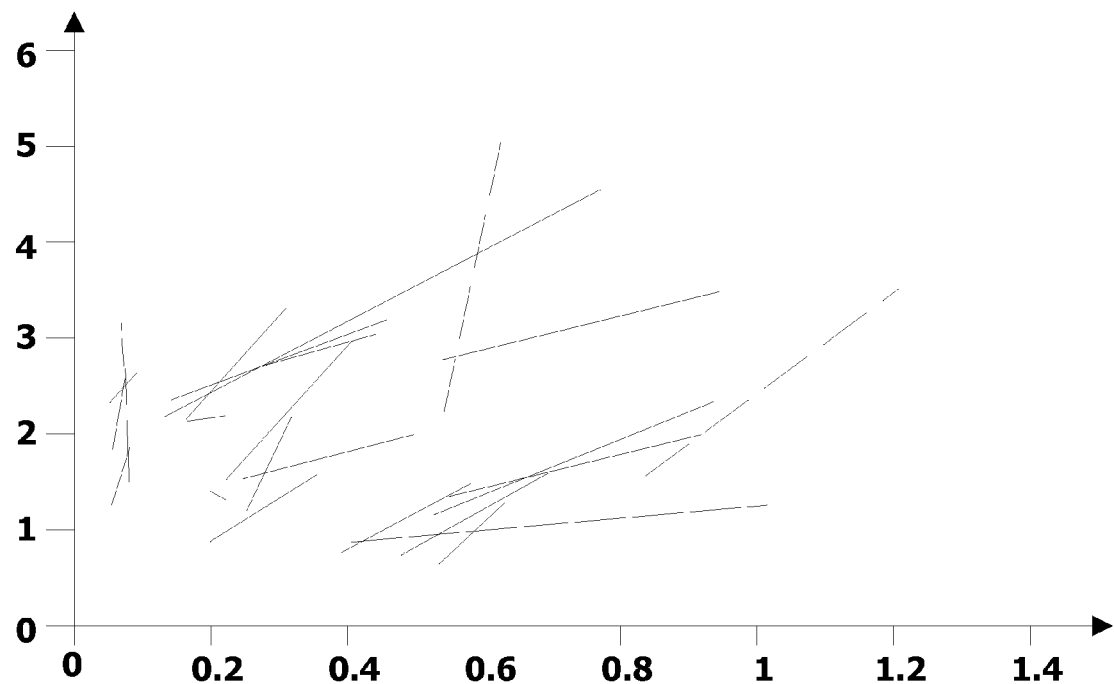
FIG. 9A is a graph illustrating the results of experimental studies on the relationship of relaxation time and saliva quantity.

The data is based on 44 tests with 13 subjects. The results (FIG. 9A) showed that relaxation time was directly related to saliva quantity for 11 of the 13 subjects. Higher relaxation times reflected increased saliva. The average gradient was approximately 2.5 sec/g saliva. The two subjects with deviant results were "very dry". The dotted lines in the graph represent tests performed after drinking water.

Figure 9B:
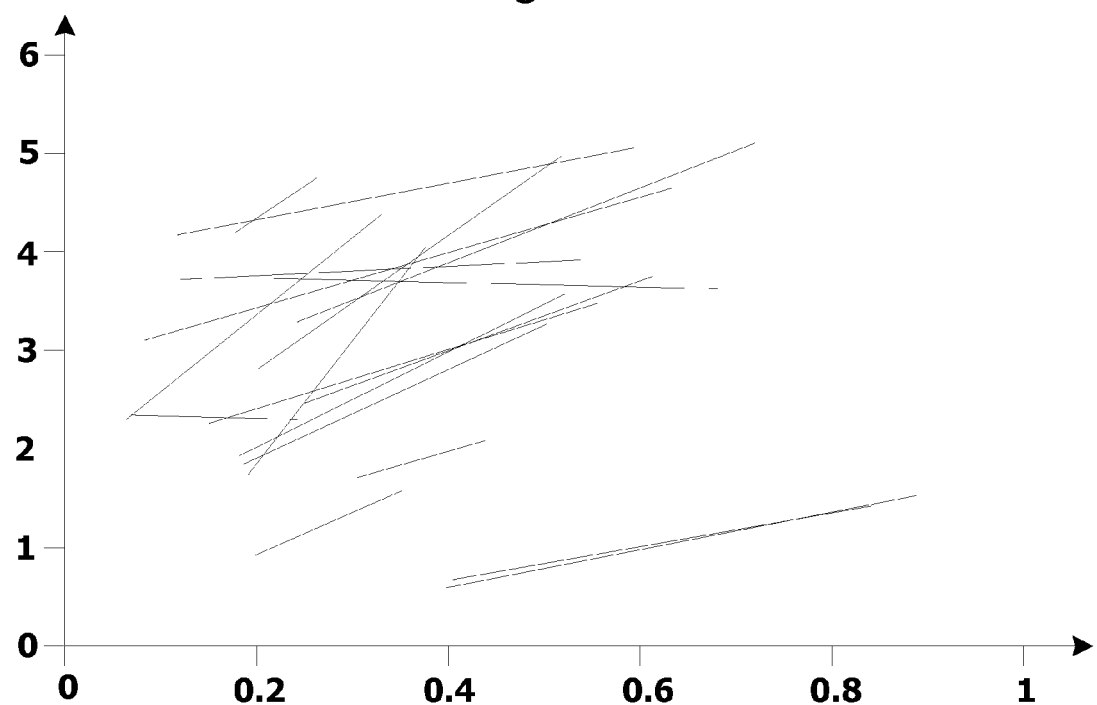
FIG. 9B is a graph illustrating the results of repeated detailed experimental studies on the relationship of relaxation time and saliva quantity in one subject.

A detailed analysis of repeated measurements was done for one subject as shown graphically in FIG. 9B. Higher relaxation time was related to increased saliva in 16 of the 18 measurements. The gradient ranged between 1.8 and 6 sec/g saliva with a mean of 2.5 sec/g saliva.

What is claimed is:

1. A system for electrically detecting a lack of saliva in an oral cavity of an individual and for electrically stimulating the oral cavity, so as to induce production of saliva from at least one salivary gland, said system comprising:
    a control device for detecting a measure of salivation in the individual and for delivering electrical impulses to the oral cavity of the individual, said control device having at least one pair of electrodes provide a contact with a tissue of the oral cavity;
    a check device for obtaining the data of said measure of salivation and for modifying at least one parameter of said control device, and
    a computer device for exchanging information with said check device;
wherein said measure of salivation is a relaxation time, said relaxation time being a measure of time required for a voltage difference between said at least one pair of electrodes to reach a predetermined level of an initial value of said voltage difference after a measuring pulse is applied.

2. The system as in claim 1, wherein said predetermined level is selected from the group consisting of 40% and 50%.

3. A device for electrically detecting a measure of saliva in an oral cavity of an individual and for delivering electrical impulses to the oral cavity of the individual so as to induce production of saliva from at least one salivary gland, said device comprising:
    a hermetically sealed housing fixable within the oral cavity;
    an electrical utility enclosed within said housing for detecting an input signal for detection of the measure of salivation and for generating the electrical impulses, said electrical utility including a power source and a signal generator, and
    at least one pair of electrodes electrically coupled to said electrical utility, wherein said at least one pair of electrodes provide a contact with a tissue of the oral cavity;
wherein said measure of salivation is a relaxation time, said relaxation time being a measure of time required for a voltage difference between said at least one pair of electrodes to reach a predetermined level of an initial value of said voltage difference after a measuring pulse is applied.

4. The device as in claim 3, wherein said predetermined level is selected from the group consisting of 40% and 50%.

5. A method for electrical stimulation of salivation comprising the steps of:
    attaching a device for electrically detecting a measure of saliva in an oral cavity of an individual and for delivering electrical impulses to said oral cavity of said individual so as to induce production of saliva from at least one salivary gland, said device having at least one pair of electrodes, said electrodes being placed against a tissue of said oral cavity;
    detecting an input signal indicative of said measure of moisture within said oral cavity;
    comparing said measure to a moisture limit value, and
    delivering said electrical impulses based on a result of said comparing;
wherein said measure of salivation is a relaxation time, said relaxation time being a measure of time required for a voltage difference between said at least one pair of electrodes to reach a predetermined level of an initial value of said voltage difference after a measuring pulse is applied.

* * * * *